US007238719B2

(12) United States Patent
Yasuda et al.

(10) Patent No.: US 7,238,719 B2
(45) Date of Patent: Jul. 3, 2007

(54) PROCESS FOR PRODUCING 1,2,3-TRIAZOLE COMPOUNDS

(75) Inventors: Shohei Yasuda, Kanagawa-Ken (JP); Koreaki Imura, Kanagawa-Ken (JP); Yumiko Okada, Kanagawa-Ken (JP); Shinichiro Tsujiyama, Kanagawa-Ken (JP)

(73) Assignee: Meiji Seika Kaisha, Ltd., Tokyo-to (JP)

( * ) Notice: Subject to any disclaimer, the term of this patent is extended or adjusted under 35 U.S.C. 154(b) by 312 days.

(21) Appl. No.: 10/502,392

(22) PCT Filed: Feb. 3, 2003

(86) PCT No.: PCT/JP03/01062

§ 371 (c)(1), (2), (4) Date: Jul. 26, 2004

(87) PCT Pub. No.: WO03/064400

PCT Pub. Date: Aug. 7, 2003

(65) Prior Publication Data

US 2005/0080270 A1    Apr. 14, 2005

(30) Foreign Application Priority Data

Feb. 1, 2002 (JP) ............................. 2002-024900

(51) Int. Cl.
*A61K 31/41* (2006.01)
*C07D 249/04* (2006.01)

(52) U.S. Cl. ..................................... 514/359; 548/255
(58) Field of Classification Search ................ 514/359; 548/255
See application file for complete search history.

(56) References Cited

U.S. PATENT DOCUMENTS

| | | | |
|---|---|---|---|
| 5,840,895 A * | 11/1998 | Ohtsuka et al. | 544/366 |
| 6,093,714 A * | 7/2000 | Ohtsuka et al. | 514/215 |
| 6,372,735 B1 * | 4/2002 | Ohtsuka et al. | 514/212.06 |
| 7,022,860 B2 * | 4/2006 | Ohtsuka et al. | 548/255 |

FOREIGN PATENT DOCUMENTS

| | | |
|---|---|---|
| DE | 19636122 A1 | 4/2007 |
| EP | 0727418 A1 | 8/1996 |
| EP | 1026167 | 8/2000 |
| JP | 56-127363 | 10/1981 |
| JP | 03-017069 | 1/1991 |
| JP | 2001-233767 | 8/2001 |

* cited by examiner

*Primary Examiner*—Kamal A. Saeed
*Assistant Examiner*—Susannah L. Chung
(74) *Attorney, Agent, or Firm*—Heller Ehrman LLP

(57) ABSTRACT

Disclosed is a process for efficiently producing a compound represented by formula (I):

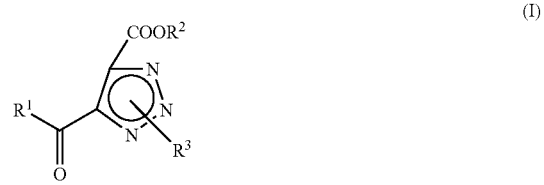

(I)

wherein $R^1$ represents aryl, amino, alkyl, or alkoxy; $R^2$ represents a protective group of the carboxylic acid; and $R^3$ represents an alkali metal, a hydrogen atom, alkyl, aryl, alkylsulfonyl, arylsulfonyl, or trialkylsilyl. This process is characterized by reacting a compound of formula (II) with a compound of formula (III) in the presence of a transition metal compound.

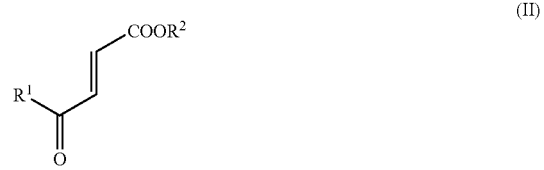

(II)

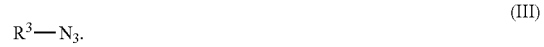

(III)

5 Claims, No Drawings

PROCESS FOR PRODUCING 1,2,3-TRIAZOLE COMPOUNDS

BACKGROUND OF THE INVENTION

1. Field of the Invention

The present invention relates to a novel process for producing 1,2,3-triazole compounds useful as a starting material or an intermediate of pharmaceutical products.

2. Background Art 1,2,3-Triazole compounds are useful as a starting material or an intermediate of pharmaceutical products. For example, the compounds can be utilized as an intermediate in the production of tricyclic triazolobenzoazepine derivatives which are useful as antiallergic agents as described in WO 99/16770. In a general production process of 1,2,3-triazole compounds, an acetylene compound or an olefin compound is reacted with an azide compound to cause a cycloaddition reaction and consequently to construct a 1,2,3-triazole ring (H. Wamhoff; "Comprehensive Heterocyclic Chemistry," Pergamon Press, New York (1984), Vol. 5, p. 705).

The cycloaddition reaction of the acetylene compound with the azide compound is highly versatile, because a wide range of substituents are accepted to both the acetylene compound and the azide compound.

On the other hand, in the cycloaddition reaction of the olefin compound with the azide compound, a special olefin compound having a leaving group such as a halogen or a hydroxyl group is provided and is aromatized by an elimination reaction (H. Wamhoff; "Comprehensive Heterocyclic Chemistry," Pergamon Press, New York (1984), Vol. 5, p. 712). The conversion to the special olefin compound is necessary for use of this cycloaddition reaction so that the production process is long. Furthermore, this cycloaddition reaction is sometimes disadvantageous in that high-temperature, high-pressure and other conditions should be used in the elimination reaction for the aromatization.

Heterocycles, vol. 51, p 481 (1999) and J. Med. Chem., vol. 26, p 714 (1983) disclose processes in which an olefin compound having no leaving group is reacted with an azide compound. This process, however, is not efficient because of low yield.

WO 99/16770 discloses a general method for converting an olefin compound to an acetylene compound. This method, however, involves a long production process and hence is cost-ineffective.

Thus, there is still a need for a process for producing a 1,2,3-triazole compound from an olefin compound having no leaving group in an efficient and cost-effective manner.

SUMMARY OF THE INVENTION

The present inventors have now found that 1,2,3-triazole compounds can be efficiently produced by directly reacting an olefin compound having no leaving group with an azide compound having a substituent in the presence of a catalytic amount of a transition metal compound. The present inventors have further found that the yield of the product can be improved by carrying out the reaction in the presence of an oxidizing agent or under an oxygen atmosphere. The present invention has been made based on such findings.

Accordingly, an object of the present invention is to provide a process which can produce a 1,2,3-triazole compound in an efficient and cost-effective manner.

According to the present invention, there is provided a process for producing a 1,2,3-triazole compound represented by formula (I):

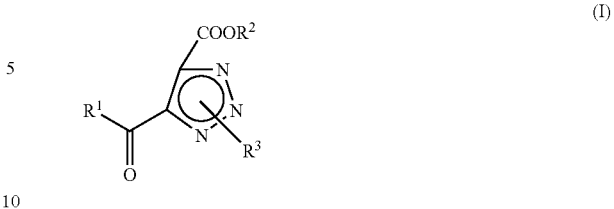

wherein $R^1$ represents optionally substituted aryl, optionally substituted amino, optionally substituted alkyl, or optionally substituted alkoxy; $R^2$ represents a protective group of the carboxylic acid; and $R^3$ represents an alkali metal, a hydrogen atom, optionally substituted alkyl, optionally substituted aryl, optionally substituted alkylsulfonyl, optionally substituted arylsulfonyl, or trialkylsilyl, the process comprising the step of:

reacting a compound represented by formula (II):

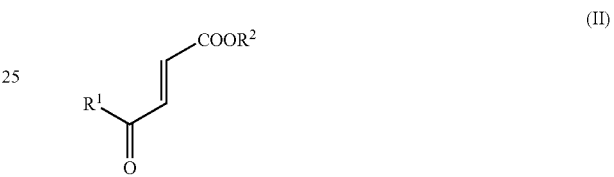

wherein $R^1$ and $R^2$ are as defined above, with an azide compound represented by formula (III):

wherein $R^3$ is as defined above, in the presence of a transition metal compound.

DETAILED DESCRIPTION OF THE INVENTION

The terms "alkyl" and "alkoxy" as used herein as a group or a part of a group respectively mean straight chain, branched chain, or cyclic alkyl and alkoxy having 1 to 6 carbon atoms, preferably 1 to 4 carbon atoms, unless otherwise specified.

The term "aryl" as used herein means phenyl or naphthyl.

Substituents as one or at least two substituents for the aryl group represented by $R^1$ include the following substituents (a) to (n):

(a) a hydrogen atom;
(b) a halogen atom;
(c) an optionally protected hydroxyl group;
(d) formyl;
(e) $C_{1-12}$ alkyl;
(f) $C_{2-12}$ alkenyl;
(g) $C_{1-12}$ alkoxy;
(h) —C=N—OR$^4$ wherein $R^4$ represents a hydrogen atom, $C_{1-6}$ alkyl, phenyl $C_{1-4}$ alkyl, or phenyl;
(i) —(CH$_2$)$_m$—OR$^5$ wherein m is an integer of 1 to 4, and $R^5$ represents a hydrogen atom, $C_{1-6}$ alkyl, or phenyl $C_{1-4}$ alkyl in which one or more hydrogen atoms on the benzene ring of the phenylalkyl group is optionally substituted by $C_{1-4}$ alkyl;
(j) —(CH$_2$)$_k$—COR$^6$ wherein k is an integer of 0 to 4, and $R^6$ represents a hydrogen atom or $C_{1-4}$ alkyl;

(k) —$(CH_2)_j$—$COOR^7$ wherein j is an integer of 0 to 4, and $R^7$ represents a hydrogen atom or $C_{1-6}$ alkyl;

(l) —$(CH_2)_p$—$NR^8R^9$ wherein p is an integer of 1 to 4, and $R^8$ and $R^9$, which may be the same or different, represent (1) a hydrogen atom, (2) $C_{1-6}$ alkyl in which the alkyl group is optionally substituted by amino optionally substituted by $C_{1-4}$ alkyl, (3) phenyl $C_{1-4}$ alkyl, (4) —$COR^{14}$ wherein $R^{14}$ represents a hydrogen atom or $C_{1-4}$ alkyl which is optionally substituted by carboxyl, or (5) —$SO_2R^{15}$ wherein $R^{15}$ represents $C_{1-4}$ alkyl or phenyl in which the phenyl group is optionally substituted by a halogen atom;

(m) —$(CH_2)_q$—$CONR^{10}R^{11}$ wherein q is an integer of 0 to 4, and $R^{10}$ and $R^{11}$, which may be the same or different, represent a hydrogen atom; a saturated or unsaturated five- to seven-membered heterocyclic ring in which the heterocyclic ring is selected from the group consisting of pyridine, imidazole, oxazole, thiazole, pyrimidine, furan, thiophene, pyrrole, pyrrolidine, piperidine, tetrahydrofuran, and oxazoline; or $C_{1-6}$ alkyl in which the alkyl group is optionally substituted by a saturated or unsaturated five- to seven-membered heterocyclic ring in which the heterocyclic ring is selected from the group consisting of pyridine, imidazole, oxazole, thiazole, pyrimidine, furan, thiophene, pyrrole, pyrrolidine, piperidine, tetrahydrofuran, and oxazoline; or alternatively $R^{10}$ and $R^{11}$ may form, together with a nitrogen atom to which they are attached, a saturated or unsaturated five- to seven-membered heterocyclic ring in which the heterocyclic ring is selected from the group consisting of pyridine, imidazole, oxazole, thiazole, pyrimidine, furan, thiophene, pyrrole, pyrrolidine, piperidine, tetrahydrofuran, oxazoline, piperazine, morpholine, succinimide, indole, isoindole, phthalimido, benzothiazole, and 1,1-dioxo-benzothiazole, and is optionally substituted by $C_{1-4}$ alkyl; and (n) —$NR^{12}R^{13}$ wherein $R^{12}$ and $R^{13}$, which may be the same or different, represent a hydrogen atom or —$COR^{16}$ wherein $R^{16}$ represents a hydrogen atom; $C_{1-6}$ alkyl; or phenyl which is optionally substituted by $C_{1-4}$ alkyl or $C_{1-6}$ alkoxy in which the alkoxy group is optionally substituted by phenyl.

Substituents as one or at least two substituents for the amino group represented by $R^1$ include: alkyl; aryl; acyl, preferably alkylcarbonyl; and optionally substituted sulfonyl, for example, alkyl optionally substituted by phenyl.

Substituents as one or at least two substituents for the alkyl group represented by $R^1$ include: straight chain alkyl, for example, methyl, ethyl, n-propyl, n-butyl, n-pentyl, and n-hexyl; branched chain alkyl, for example, isopropyl, isobutyl, tert-butyl, and 3-pentyl; and cyclic $C_{3-7}$ alkyl, for example, cyclopropyl, cyclobutyl, cyclopentyl, and cyclohexyl.

Substituents as one or at least two substituents for the alkoxy group represented by $R^1$ include: halogen atoms; hydroxyl; cyano; $C_{3-7}$ cycloalkyl; phenyl; $C_{1-4}$ alkoxy; phenoxy; and amino which is optionally substituted by $C_{1-4}$ alkyl.

In a preferred embodiment of the present invention, $R^1$ represents phenyl, 3-methoxyphenyl, 4-methoxyphenyl, 3,4-dimethoxyphenyl, 6-amino-3,4-dimethoxyphenyl, 3,4-dimethoxy-phenylamino, ethoxyl, or methoxyl, more preferably 3,4-dimethoxyphenyl, 3,4-dimethoxy-phenylamino, or methoxyl.

In the present invention, preferred protective groups of the carboxylic acid represented by $R^2$ include, for example, methyl, ethyl, tert-butyl, benzyl, 4-methoxybenzyl, diphenylmethyl, 4-nitrobenzyl, tert-butyldimethylsilyl, triphenylsilyl, 2-phenylsulfonylethyl, 2-methoxycarbonylethyl, 2-cyanoethyl, and 2-trimethylsilylethyl, more preferably methyl, ethyl, tert-butyl, benzyl, 4-methoxybenzyl, diphenylmethyl, 4-nitrobenzyl, tert-butyldimethylsilyl, triphenylsilyl, 2-phenylsulfonylethyl, 2-methoxycarbonylethyl, 2-cyanoethyl, and 2-trimethylsilylethyl, particularly preferably ethyl.

In the present invention, substituents for the alkyl, alkylsulfonyl, and arylsulfonyl groups represented by $R^3$ include phenyl optionally substituted by nitro or alkoxy.

Examples of preferred groups as $R^3$ include methyl, ethyl, benzyl, p-nitrobenzyl, p-methoxybenzyl, methylsulfonyl, ethylsulfonyl, benzylsulfonyl, p-nitrobenzylsulfonyl, p-methoxybenzylsulfonyl, phenyl, p-methoxyphenyl, p-nitrophenyl, naphthyl, trimethylsilyl, triethylsilyl, tert-butyldimethylsilyl, triphenylsilyl, tert-butyidiphenylsilyl, alkali metal, and a hydrogen atom, more preferably sodium, potassium, a hydrogen atom, trimethylsilyl, triethylsilyl, t-butyidimethylsilyl, p-methoxybenzyl, and toluenesulfonyl, particularly preferably sodium and a hydrogen atom.

Reaction Conditions

While in the present invention proportions of the compounds used are not particularly limited and may be properly determined, the amount of the azide compound of formula (III) used is preferably 0.5 to 20 molar equivalents, more preferably 1 to 3 molar equivalents, based on the compound of formula (II). The reaction is carried out in a suitable solvent at room temperature or with heating. The solvent usable in the reaction is not particularly limited so far as the solvent does not retard the progress of the reaction, and examples thereof include: alkyl alcohols such as methanol, ethanol, isopropanol and butanol; alkyl ethers such as tetrahydrofuran, dioxane and diphenyl ether; halogenated hydrocarbons such as methylene chloride, chloroform, and 1,1,2,2-tetrachloroethane; aromatic hydrocarbons such as benzene, toluene and xylene; ketones such as acetone and 2-butanone; aprotic polar solvents such as N,N-dimethylformamide, dimethylsulfoxide, and acetonitrile; or water. These solvents may be used solely or as a mixture of two or more. The reaction temperature is preferably –20° C. to the boiling point of the solvent, more preferably 0° C. to the boiling point of the solvent. The reaction time is preferably 10 min to 48 hr, more preferably 2 to 15 hr.

Transition Metal Compound

In the present invention, the transition metal compound used in the reaction is preferably copper(I) chloride, copper (I) bromide, copper(I) iodide, iron(III) bromide, iron(III) chloride and iron(III) iodide, more preferably copper(I) chloride and iron(III) chloride. Further, hydrates of these compounds may also be used.

Oxidizing Agents

The process according to the present invention, when carried out in the presence of an oxidizing agent, can provide compounds of formula (I) in improved yields, and, hence, the utilization of the oxidizing agent is preferred. Preferred oxidizing agents include, for example, salts of halogen oxy-acids such as chlorate, chlorite, bromate and iodate, organic peracids such as persulfate, hydrogen peroxide, peracetic acid and 4-chloroperbenzoic acid and metallic oxides such as manganese deoxide and chromic acid. More preferred are sodium chlorate and sodium bromate. The amount of the oxidizing agent used is preferably 0.1 to 5 molar equivalents, more preferably 0.4 to 1.5 molar equivalents, based on the compound of formula (II). The utilization of oxygen can also provide compounds of formula (I) in improved yields. In this case, preferably, the reaction is carried out under an oxygen atmosphere until the reaction is completed, or alternatively the supply of oxygen into the reaction solution is continued until the reaction is completed.

Optionally after reaction terminating treatment, the compound produced by the process of the present invention can be easily purified by conventional purification methods such as recrystallization, chromatography, and distillation.

EXAMPLES

The present invention is further illustrated by the following Examples that are not intended as a limitation of the invention.

Example 1

Ethyl 5-(3,4-dimethoxybenzoyl)-1H-1,2,3-triazole-4-carboxylate

Copper(I) chloride (7.5 mg, 0.075 mmol) was added at room temperature to a solution (1.0 mL) of sodium azide (74 mg, 1.1 mmol) in N,N-dimethylformamide. A solution (1.5 mL) of ethyl 4-(3,4-dimethoxyphenyl)-4-oxo-2-butenate (200 mg, 0.76 mmol) in N,N-dimethylformamide was added to this mixed solution at 5° C. The temperature of the reaction solution was raised to room temperature before the reaction solution was stirred for 8 hr. After the completion of the reaction, the reaction solution was poured into iced water, and the mixture was extracted with a saturated aqueous sodium hydrogencarbonate solution. The aqueous layer was adjusted to pH 1.8 by the addition of 2 N hydrochloric acid, followed by extraction with ethyl acetate. The organic layer was dried over anhydrous sodium sulfate, and the solvent was then removed by evaporation under the reduced pressure. The oil thus obtained was dried in vacuo to give ethyl 5-(3,4-dimethoxybenzoyl)-1H-1,2,3-triazole-4-carboxylate (149 mg, 65%).

$^1$H-NMR (CDCl$_3$): δ 1.70 (3H, t), 3.90 (3H, s), 3.93 (3H, s), 4.28 (2H, q), 6.84 (1H, d), 7.39 (1H, dd), 7.60 (1H, d).
$^{13}$C-NMR (CDCl$_3$): δ 13.9, 56.1, 56.2, 62.2, 109.9, 110.8, 126.3, 129.3, 149.1, 154.3, 160.1, 185.8.

Example 2

Ethyl 5-(3,4-dimethoxybenzoyl)-1H-1,2,3-triazole-4-carboxylate

Copper(I) chloride (190 mg, 1.91 mmol) was added at room temperature to a solution (40 mL) of sodium azide (1.84 g, 28.3 mmol) in N,N-dimethylformamide, and the air in the system was replaced by oxygen. A solution (10 mL) of ethyl 4-(3,4-dimethoxyphenyl)-4-oxo-2-butenoate (2.50 g, 9.46 mmol) in N,N-dimethylformamide was added to this mixed solution at 5° C. over a period of 30 min. The temperature of the reaction solution was raised to room temperature before the reaction solution was stirred for 3 hr. Thereafter, the reaction temperature was lowered to 5° C., and a solution (10 mL) of ethyl 4-(3,4-dimethoxyphenyl)-4-oxo-2-butenoate (2.50 g, 9.46 mmol) in N,N-dimethylformamide was added thereto. The temperature of the reaction solution was raised to room temperature before the reaction solution was stirred for 4 hr. After the completion of the reaction, the reaction solution was poured into iced water (75 mL), and sodium nitrite (636 mg, 9.22 mmol) was added thereto. The mixture was adjusted to pH 1.8 by the addition of 6 N sulfuric acid and was extracted with ethyl acetate. To the organic layer was added 5 wt % brine. The mixture was adjusted to pH 1.5 by the addition of 1 N hydrochloric acid, followed by separation. The organic layer was dried over anhydrous sodium sulfate, and the solvent was removed by evaporation under the reduced pressure. Toluene was added to the residue, and the solvent was removed by evaporation under the reduced pressure. The resultant crystal was washed with toluene and was then dried under the reduced pressure to give ethyl 5-(3,4-dimethoxybenzoyl)-1H-1,2,3-triazole-4-carboxylate (4.71 g, 81%).

Example 3

Ethyl 5-(3,4-dimethoxybenzoyl)-1H-1,2,3-triazole-4-carboxylate

Iron(III) chloride (309 mg, 1.90 mmol) was added at room temperature to a solution (37.5 mL) of sodium azide (1.84 g, 28.3 mmol) in N,N-dimethylformamide. A solution (25 mL) of ethyl 4-(3,4-dimethoxyphenyl)-4-oxo-2-butenoate (2.50 g, 9.46 mmol) in N,N-dimethylformamide was then added to the mixture at 5° C. under an oxygen atmosphere. The temperature of the reaction solution was raised to room temperature before the reaction solution was stirred for 3 hr. Thereafter, ethyl 4-(3,4-dimethoxyphenyl)-4-oxo-2-butenoate (2.50 g, 9.46 mmol) was added to the reaction solution at room temperature, and the mixture was stirred for additional 4 hr. After the completion of the reaction, the reaction solution was poured into iced water, and sodium nitrite (636 mg, 9.22 mmol) was added thereto. The mixture was adjusted to pH 2 by the addition of 1 N hydrochloric acid and was extracted with ethyl acetate, and 5 wt % brine was then added. The mixture was adjusted to pH 2.0 by the addition of 1 N hydrochloric acid, followed by separation. The organic layer was dried over anhydrous sodium sulfate, and the solvent was then removed by evaporation under the reduced pressure. Toluene was added to the residue, and toluene was removed by evaporation under the reduced pressure. The resultant crystal was collected by filtration, was washed with toluene, and was then dried under the reduced pressure to give ethyl 5-(3,4-dimethoxybenzoyl)-1H-1,2,3-triazole-4-carboxylate (5.08 g, 88%).

Example 4

Ethyl 5-(3,4-dimethoxybenzoyl)-1H-1,2,3-triazole-4-carboxylate

Sodium azide (4.87 g, 75 mmol), sodium chlorate (2.90 g, 27 mmol), and a 37% aqueous ferric chloride solution (1.49 g, 3 mmol) were added to N,N-dimethylformamide (36 mL), the mixed solution was heated to 40° C., and a mixed solution previously prepared by adding ethyl 4-(3,4-dimethoxyphenyl)-4-oxo-2-butenoate (18 g, 68 mmol) to N,N-dimethylformamide (36 mL) and then dissolving them each other at 50° C. was added dropwise thereto. After the completion of the dropwise addition, a reaction was allowed to proceed at 40° C. for one hr, and a reaction was further allowed to proceed at 65° C. for one hr. After the completion of the reaction, the reaction solution was cooled to 5° C., and acetonitrile (7 mL) and an aqueous solution of sodium nitrite (1.18 g, 17 mmol) in water (25 mL) were successively added dropwise thereto. The mixture was adjusted to pH 1.5 by the addition of a 3 M aqueous sulfuric acid solution. The mixture was stirred at 5° C. for one hr, and ethyl acetate (198 ml) was then added thereto, followed by separation. The organic layer was washed three times with 5% brine, was dried over anhydrous magnesium sulfate, and was filtered. The filtrate was concentrated under the reduced pressure to precipitate crystals. Toluene (90 mL) was added to the residue of the concentration, and the crystals were aged at 5° C. for 12 hr. The crystals were collected by filtration, were then washed with toluene, and were dried under the reduced pressure to give 17.15 g of a light yellow powder (yield 82.5%).

Example 5

Ethyl 1H-1,2,3-triazole-4,5-dicarboxylate

Copper(I) chloride (288 mg, 2.91 mmol) was added at room temperature to a solution (52.5 mL) of sodium azide (2.83 g, 43.5 mmol) in N,N-dimethylformamide. A solution (5.0 mL) of diethyl fumarate (2.50 g, 14.5 mmol) in N,N-dimethylformamide was added to the mixture at 5° C. under an oxygen atmosphere. The temperature of the reaction solution was raised to room temperature before the reaction solution was stirred for 12 hr. Thereafter, the reaction solution was cooled to 5° C., and a solution (5.0 mL) of diethyl fumarate (2.50 g, 14.5 mmol) in N,N-dimethylformamide was added thereto, and the temperature of the reaction solution was raised to room temperature before the reaction solution was stirred for 12 hr. After the completion of the reaction, the reaction solution was poured into iced water (75 mL), and sodium nitrite (1.00 g, 14.5 mmol) was added thereto. The mixture was adjusted to pH 1.8 by the addition of 2 N hydrochloric acid and was extracted with ethyl acetate. Saturated brine was then added to the organic layer, and the mixture was adjusted to pH 1.0 by the addition of 1 N hydrochloric acid, followed by separation. The organic layer was dried over anhydrous sodium sulfate, and the solvent was then removed by evaporation under the reduced pressure. The oil thus obtained was dried under the reduced pressure to give ethyl 1H-1,2,3-triazole-4,5-dicarboxylate (5.96 g, 96%).
$^1$H-NMR (CDCl$_3$): δ 1.39 (6H, t), 4.44 (4H, q).

Example 6

Ethyl 5-(3,4-dimethoxy-phenylcarbamoyl)-1H-1,2,3-triazole-4-carboxylate

Copper(I) chloride (35 mg, 0.35 mmol) was added at room temperature to a solution (50 mL) of sodium azide (690 mg, 10.6 mmol) in N,N-dimethylformamide, and the air in the system was replaced by oxygen. This mixed solution was cooled to 5° C., and a solution (30 mL) of ethyl 4-(3,4-dimethoxy-anilid)-4-oxo-2-butenoate (1.00 g, 3.58 mmol) in N,N-dimethylformamide was added thereto over a period of 30 min. The temperature of the reaction solution was raised to room temperature before the reaction solution was stirred for 2 days. After the completion of the reaction, the reaction solution was poured into iced water, and sodium nitrite (494 mg, 7.16 mmol) was added thereto. The mixture was adjusted to pH 1.5 by the addition of 2 N hydrochloric acid and was extracted with ethyl acetate. Saturated brine was then added to the organic layer, and the mixture was adjusted to pH 1.5 by the addition of 1 N hydrochloric acid, followed by separation. The organic layer was dried over anhydrous sodium sulfate, and the solvent was then removed by evaporation to about 20 mL under the reduced pressure. The precipitated solid was collected by filtration, was washed with ethyl acetate, and was then dried under the reduced pressure to give ethyl 5-(3,4-dimethoxy-phenylcarbamoyl)-1H-1,2,3-triazole-4-carboxylate (888 mg, 77%).
$^1$H-NMR (DMSO-d$_6$): δ 1.24 (3H, t), 3.74 (6H, s), 4.32 (2H, q), 6.94 (1H, d), 7.20 (1H, dd), 7.38 (1H, d), 10.70 (1H, br-s).

Reference Example

Ethyl 5-(3,4-dimethoxybenzoyl)-1H-1,2,3-triazole-4-carboxylate

A solution (3.0 mL) of ethyl 4-(3,4-dimethoxyphenyl)-4-oxo-2-butenoate (104 mg, 0.39 mmol) in N,N-dimethylformamide was added to a solution (5.0 mL) of sodium azide (40 mg, 0.62 mmol) in N,N-dimethylformamide at 5° C. The temperature of the reaction solution was raised to room temperature before the reaction solution was stirred for 6 hr. After the completion of the reaction, iced water (10 mL) was added to the reaction solution, and the mixture was washed with ethyl acetate. The aqueous layer was then adjusted to pH 1.5 by the addition of 2 N hydrochloric acid, followed by extraction with ethyl acetate. The organic layer was dried over anhydrous sodium sulfate, and the solvent was then removed by evaporation under the reduced pressure. The oil thus obtained was dried in vacuo to give ethyl 5-(3,4-dimethoxybenzoyl)-1H-1,2,3-triazole-4-carboxylate (63 mg, yield 52%).

What is claimed is:
1. A process for producing a 1,2,3-triazole compound represented by formula (I):

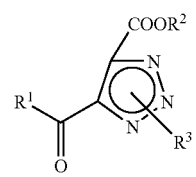

wherein R$^1$ represents optionally substituted aryl, optionally substituted amino, optionally substituted alkyl, or optionally substituted alkoxy; R$^2$ represents a protective group of the carboxylic acid; and R$^3$ represents an alkali metal, a hydrogen atom, optionally substituted alkyl, optionally substituted aryl, optionally substituted alkylsulfonyl, optionally substituted arylsulfonyl, or trialkylsilyl, said process comprising the step of: reacting a compound represented by formula (II):

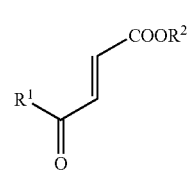

wherein R$^1$ and R$^2$ are as defined above, with an azide compound represented by formula (III):

wherein R$^3$ is as defined above, in the presence of a transition metal compound.

2. The process according to claim 1, wherein the transition metal compound is copper(I) chloride or iron(III) chloride.

3. The process according to claim 1 or 2, wherein the reaction is carried out in the presence of an oxidizing agent or under an oxygen atmosphere.

4. The process according to claim 3, wherein the oxidizing agent is sodium chlorate or sodium bromate.

5. The process according to any one of claims 1 to 4, wherein $R^1$ represents 3,4-dimethoxyphenyl, 3,4-dimethoxy-phenylamino, or methoxyl, $R^2$ represents ethyl, and $R^3$ represents sodium or a hydrogen atom.

* * * * *